United States Patent [19]

Lantzsch et al.

[11] B 4,001,250

[45] Jan. 4, 1977

[54] PROCESS FOR PREPARING 4-AMINO-2,2,6,6-TETRAMETHYL PIPERIDINE

[75] Inventors: Reinhard Lantzsch; Dieter Arlt, both of Cologne, Germany

[73] Assignee: Bayer Aktiengesellschaft, Leverkusen, Germany

[22] Filed: Feb. 24, 1975

[21] Appl. No.: 552,508

[44] Published under the second Trial Voluntary Protest Program on March 16, 1976 as document No. B 552,508.

[30] Foreign Application Priority Data

Mar. 16, 1974 Germany .................... 2412750

[52] U.S. Cl. ............................................ 260/293.52
[51] Int. Cl.$^2$ ..................................... C07D 211/58

[58] Field of Search ................. 260/293.52, 293.87

[56] References Cited

OTHER PUBLICATIONS

Paden et al., J. Am. Chem. Soc. 58, 2487–2499 (1936).

*Primary Examiner*—G. Thomas Todd
*Attorney, Agent, or Firm*—Burgess, Dinklage & Sprung

[57] ABSTRACT

4-amino-2,2,6,6-tetramethyl piperidine is prepared by reacting phorone with ammonia and hydrogen in the presence of a hydrogenation catalyst. The reaction is generally carried out at a temperature in the range of from 80° to 200° C and under a pressure of from 80 to 250 atmospheres.

9 Claims, No Drawings

PROCESS FOR PREPARING 4-AMINO-2,2,6,6-TETRAMETHYL PIPERIDINE

BACKGROUND

This invention relates to a new process for the production of 4-amino-2,2,6,6-tetramethyl-piperidine by the reductive amination of phorone.

It is already known that 4-amino-2,2,6,6-tetramethyl piperidine can be obtained in accordance with the following reaction scheme:

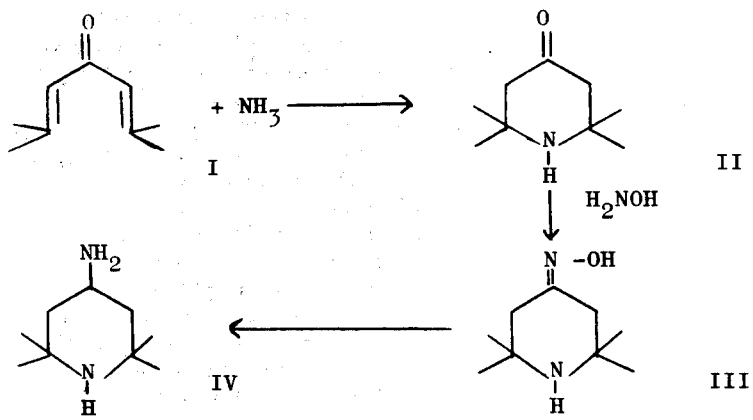

Phorone (I) is condensed with ammonia to form 2,2,6,6-tetramethyl-4-piperidone ["triacetone amine"-](II), cf. Pharm. Chem. J. 1971, page 44 and Bull. Soc. chim. France 1958, pages 345 to 346. The triacetone amine is then reacted with hydroxylamine to form the oxime (III) (cf. Berichte der Deutschen Chemischen Gesellschaft, vol. 29, page 53 (1896) and Bull Soc. chim. France 1965, page 3282), from which the 4-amino-2,2,6,6-tetramethyl piperidine (IV) is obtained by reduction with zinc/hydrochloric acid or metallic sodium in amyl alcohol (cf. Liebigs Ann. d. Chemie, vol. 417, pages 118 to 119 (1918) and Izv. Akad. Nauk. SSSR Ser. Khim. 1966, page 1477).

Unfortunately, the total yield of this synthesis which involves 3 steps only amounts to about 30%, and furthermore a number of byproducts are inevitably formed. Accordingly, there is a considerable need for a commercially favourable process for the production of 4-amino-2,2,6,6-tetramethyl piperidine.

SUMMARY

It has now been found that 4-amino-2,2,6,6-tetramethyl piperidine can be obtained in high yields by treating phorone with ammonia and hydrogen in the presence of hydrogenation catalysts.

DESCRIPTION

The process according to the invention may be regarded as reductive amination and may be schematically illustrated by the following reaction equation:

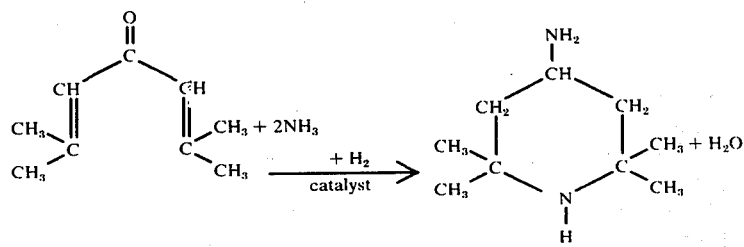

In general, at least 2 moles of ammonia are used per one mole of phorone in accordance with the above reaction equation. However, it is also possible to use an excess of ammonia of up to 10 moles, more especially from 6 to 8 moles, over and above the stoichiometrically necessary quantity of 2 moles of ammonia. Although an even larger excess of ammonia is harmless, it is generally uneconomical and not advisable.

In general, at least 1 mole of hydrogen is used per 1 mole of phorone in accordance with the above reaction equation. In most cases, however, the hydrogen is used in an excess over and above the minimum stoichiometrically necessary quantity. The quantity of hydrogen used is preferably such that the pressure range selected for carrying out the reaction is reached. However, hydrogen may even be diluted with a gas which is inert under the reaction conditions, such as nitrogen, in order to reach this pressure.

In general, the process according to the invention is carried out at an elevated temperature, preferably at a temperature in the range from 80° to 200°C, more especially at a temperature in the range from 110° to 150°C, and under elevated pressure, preferably under a pressure in the range of from 80 to 250 atms more especially in the range from 100 to 180 atms.

However, the reaction may also be carried out at temperatures and pressures outside the preferred range. In that case, however, the reaction time is generally longer, the yield lower and more byproducts are formed.

The process according to the invention may be carried out either in the presence or in the absence of a solvent. The presence of a solvent can be of advantage.

Examples of suitable solvents include straight-chain and branched aliphatic and cycloaliphatic hydrocarbons having 5 to 20 preferably 5 to 8 carbon atoms, such as hexane, isooctane, cyclopentane, cyclohexane; aryl and aralkyl hydrocarbons having 6 to 20 carbon atoms, preferably having 6 to 12 carbon atoms, such as benzene, toluene, xylene, propyl benzene, isopropyl benzene; aliphatic ethers having 3 to 20, preferably having 3 to 10 carbon atoms, such as propyl ether, isopropyl ether, butyl ether, isobutyl ether, amyl ether; cyclic ethers having 3 to 10 carbon atoms such as tetrahydrofuran, dioxan; lower aliphatic alcohols having 1 to 6, preferably having 1 to 4 carbon atoms, such as methanol, ethanol, propanol, ispropanol, butanol, isobutanol, tert.-butanol; cycloaliphatic alcohols such as cyclopentanol, cyclohexanol and methyl cyclohexanol.

It is preferred to use lower aliphatic alcohols, especially methanol.

In general, the solvent is used in a quantity of from about 0.5 to about 4 g and preferably in a quantity of approximately 2 g per g of phorone. However, it is also possible to use larger quantities of the solvent.

Suitable hydrogenation catalysts are hydrogenation catalysts known per se, such as metals and compounds of the metals of the Eighth Secondary Group of the Periodic System of the Elements (iron, cobalt, nickel, ruthenium, rhodium, palladium, osmium, iridium, platinum), also chromium, manganese, copper, zinc, molybdenum, tungsten, rhenium and copper chromite. It is possible in particular to use the metals nickel, cobalt, iron and the platinum metals.

The aforementioned hydrogenation catalysts may of course be used both without supports and also in the form of supported catalysts. Suitable catalyst supports include conventional materials such as carbon, silica and silicates in the usual form, for example in the form of powder or in the form of shaped particles such as beads and slugs or the like. The usual Raney catalysts, more especially Raney nickel and Raney cobalt, also platinum or carbon as support, may be used with advantage in the process according to the invention.

The quantity in which the catalyst is used is not a critical parameter of the process according to the invention, being of the order normally used for reductions with catalysts of the Raney type. In general, the catalyst is used in quantities of from about 1 to 30% by weight and more especially in quantities of from about 10 to about 20% by weight based on phorone. It is also possible to use smaller or larger quantities of catalyst, although this is not generally advisable because, where smaller quantities of catalyst are used, the reaction times become longer, whilst where larger quantities of catalyst are used the consumption of catalyst is unnecessarily high in view of the batch-style working of the process according to the invention.

The process according to the invention can of course also be carried out continuously. The individual process features and apparatus required for continuous working are known to the expert from the prior art.

In the process according to the invention, acetic acid, ammonium acetate or ammonium chloride may advantageously be added to the reaction mixture in a quantity of about 1% by weight, based on the phorone used, in order to prevent possible reduction of the keto group of the phorone into the corresponding alcohol group (cf. Houben-Weyl, Methoden der organischem Chemie, 4th edition, vol XI/I, page 611). However, it has been found that, in the process according to the invention, the advantage of suppressing a possible secondary reaction is generally limited and produces only a slight increase in yield. In general, no serious disadvantages are incurred by omitting this addition.

The process according to the invention is generally carried out by introducing the catalyst, ammonia and solvent, if any, and adding the phorone, optionally in solution in a solvent, with thorough mixing at the reaction temperature and reaction pressure, i.e. hydrogen pressure, selected. The reaction time is from about 1 to about 4 hours and is of course governed both by the quantity of starting material used and of course by the other reaction parameters. The end of the reaction is reached when hardly any more hydrogen is being taken up, and may be detected in known manner by conventional analytical methods.

The technical advance of the process according to the invention over the prior art lies in the considerably better yield and in the fact that the process is easier to carry out insofar as it only comprises one step. Apart from the starting material of the conventional multi-stage synthesis, namely, phorone and ammonia, the single-stage process according to the invention uses only hydrogen and conventional hydrogenation catalysts, but no other auxiliaries which would only give rise to the formation of troublesome byproducts. In addition, it is surprising that the process according to the invention can be carried out at all, because according to Houben-Weyl, Methoden der organischen Chemie, 4th edition, vol XI/I, pages 611 to 617, the reductive amination of phorone, accompanied by hydrogenation of the double bonds, should have resulted inter alia in the formation of 2-isobutyl-4-methyl butyl amine.

By contrast, the only secondary product formed in the process according to the invention is isopropyl amine, apart of course from the main product 4-amino-2,2,6,6-tetramethyl piperidine. However, if the process according to the invention is carried out at temperatures below the preferred range, not only 2-isobutyl-4-methyl butyl amine but also other byproducts are obtained in relatively large quantities. For example, 2-isobutyl-4-methyl butyl amine is formed in a quantity of 19% by weight of the reaction product where the process according to the invention is carried out at 60°C/150 atms hydrogen pressure.

Phorone is prepared by reacting acetone with hydrochloric acid (Liebigs Ann.d.Chemie, vol. 140,297,301).

4-Amino-2,2,6,6-tetramethyl piperidine is a valuable intermediate product for the production of compounds which are used for stabilising synthetic polymers (German Offenlegungsschrift No.2,040,975).

EXAMPLE 1

100 ml of methanol, 150 ml (approximately 6 moles) of liquid ammonia and 1 ml of acetic acid, together with 20 g of a standard hydrogenation catalyst (Raney cobalt), were introduced into a 0.7 litre capacity hydrogenation autoclave. The autoclave was then heated to a temperature of approximately 110°C and the hydrogen pressure maintained in the range from 130 to 150 atms. After the prescribed hydrogenation temperature of 110°C had been reached, a solution of 100 g (0.725 mol) of phorone in 100 ml of methanol was pumped in over a period of 1 hour. Hydrogenation was over after about another hour. After cooling, the autoclave was vented, the reaction solution filtered off from the catalyst and subjected to fractional distillation, yielding 72.5 g (64% of the theoretical yield) of 4-amino-2,2,6,6-tetramethyl piperidine with a boiling point of 88°–92°C/16 Torr.

EXAMPLE 2

100 ml of methanol, 150 ml of liquid ammonia, 1 ml of acetic acid and 20 g of a standard commercial hydrogenation catalyst (Raney nickel) were introduced into a 0.7 litre capacity autoclave. The autoclave was heated to a hydrogenation temperature of 110°C under a hydrogen pressure of 130 to 150 atms, after which a solution of 100 g of phorone in 100 ml of methanol was pumped in over a period of approximately 1 hour. Hydrogenation was over after about another hour. After cooling, the autoclave was vented, the reaction solution filtered off from the catalyst and subjected to fractional distillation, yielding 61 g (54% of the theoretical yield) of 4-amino-2,2,6,6-tetramethyl piperidine with a boiling point of 89°–95°C/18 Torr.

EXAMPLE 3

100 ml of methanol, 150 ml of liquid ammonia, 1 ml of acetic acid and 20 g of a standard commercial hydrogenation catalyst (Raney cobalt), were introduced into a 0.7 litre capacity hydrogenation autoclave. The autoclave was heated to the hydrogenation temperature of approximately 150°C under a hydrogen pressure of approximately 100 atms, after which a solution of 100 g of phorone in 100 ml of methanol was pumped in over a period of about 1 hour. Hydrogenation was complete after about another hour. After cooling, the autoclave was vented, the reaction solution filtered off from the catalyst and subjected to fractional distillation, yielding 80 g (71% of the theoretical yield) of 4-amino-2,2,6,6-tetramethyl piperidine with a boiling point of 82°–88°C/15 Torr.

EXAMPLE 4

100 ml of methanol, 110 ml (approximately 4 moles) of liquid ammonia, 1 ml of acetic acid and 15 g of standard commercial hydrogenation catalyst (Raney cobalt) were introduced into a 0.7 litre capacity hydrogenation autoclave. The autoclave was heated to 80°C under a hydrogen pressure of about 80 to 100 atms, after which the hydrogen pressure was kept at around 180 atms. A solution of 100 g of phorone in 100 ml of methanol was pumped in over a period of about 1 hour. Hydrogenation was over after about 45 minutes. After cooling, the autoclave was vented, the reaction solution was filtered off from the catalyst and subjected to fractional distillation, yielding 43 g (38% of the theoretical yield) of 4-amino-2,2,6,6-tetramethyl piperidine with a boiling point of 82°–92°C/15–16 Torr.

EXAMPLE 5

100 ml of methanol, 150 ml of liquid ammonia, 1 g of ammonium chloride and 20 g of a standard commercial hydrogenation catalyst (Raney nickel) were introduced into a 0.7 litre capacity hydrogenation autoclave. The autoclave was heated to 200°C under a hydrogen pressure of about 20 to about 40 atms, so that the hydrogen pressure settled at a level of approximately 80 atms. A solution of 100 g of phorone in 100 ml of methanol was then pumped in over a period of about 1 hour. After about 30 minutes, the fall in the hydrogen pressure and, hence, hydrogenation were over. After cooling, the autoclave was vented and the reaction solution filtered off from the catalyst. Fractional distillation of the reaction solution yielded 52 g (46% of the theoretical yield) of 4-amino-2,2,6,6-tetramethyl piperidine with a boiling point of 86° to 90°C/15 Torr.

EXAMPLE 6

100 ml of methanol, 110 ml of liquid ammonia, 1 ml of acetic acid and 20 g of a standard commercial hydrogenation catalyst (Raney cobalt) were introduced into a 0.7 litre capacity hydrogenation autoclave, after which the autoclave was heated to approximately 80°C under a hydrogen pressure of approximately 100 atms. The hydrogen pressure was then increased to 250 atms, and a solution of 100 g of phorone in 100 ml of methanol was pumped in over a period of about 1 hour, during which the hydrogen pressure was kept between 225 and 250 atms. Hydrogenation was over after about 20 minutes. The reaction solution was then filtered off from the catalyst and subjected to fractional distillation, yielding 47 g (41.5% of the theoretical yield) of 4-amino-2,2,6,6-tetramethyl piperidine with a boiling point of 80° to 91°C/16–18 Torr.

EXAMPLE 7

100 ml of methanol, 150 ml of liquid ammonia, 1 ml of acetic acid and 15 g of Raney cobalt were introduced into a 0.7 litre capacity hydrogenation autoclave. The autoclave was heated to approximately 180°C under a hydrogen pressure of 80 to 100 atms, after which a solution of 100 g of phorone in 100 ml of methanol was pumped in over a period of 1 hour. After about 30 minutes, the fall in pressure and, hence, hydrogenation was over. After cooling, the autoclave was vented and the reaction solution filtered off from the catalyst and subjected to fractional distillation, yielding 74 g (65.5% of the theoretical yield) of 4-amino-2,2,6,6-tetramethyl piperidine with a boiling point of 90° to 93°C/18 Torr.

What is claimed is:

1. Process for preparing 4-amino-2,2,6,6-tetramethyl piperidine which comprises reacting phorone with ammonia and hydrogen in the presence of a hydrogenation catalyst.
2. Process of claim 1 wherein the reaction is carried out at elevated temperatures and pressures.
3. Process of claim 1 wherein the reaction is carried out at a temperature in the range from 80° to 200°C.
4. Process of claim 1 wherein the reaction is carried out at a pressure in the range from 80 to 250 atms.
5. Process of claim 1 wherein the reaction is carried out in the presence of a solvent.
6. Process of claim 5, wherein methanol is the solvent.
7. Process of claim 1 wherein the ammonia is used in an excess of 6 to 8 mols per mol of phorone.
8. Process of claim 1 wherein the hydrogen is used in excess.
9. Process of claim 1 wherein the hydrogenation catalyst is selected from the group of nickel, cobalt, iron and platinum.

* * * * *